(12) United States Patent
Sola et al.

(10) Patent No.: US 6,214,860 B1
(45) Date of Patent: *Apr. 10, 2001

(54) SYNERGISTIC ANTITUMOR COMPOSITION CONTAINING A NAPHTHALENSULPHONIC ACID DERIVATIVE

(75) Inventors: Francesco Sola, Seregno; Maria Grandi, Reggio Emilia, both of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/367,853

(22) PCT Filed: Dec. 12, 1998

(86) PCT No.: PCT/EP98/08159

§ 371 Date: Aug. 30, 1999

§ 102(e) Date: Aug. 30, 1999

(87) PCT Pub. No.: WO99/34796

PCT Pub. Date: Jul. 15, 1999

(30) Foreign Application Priority Data

Dec. 31, 1997 (GB) .................................... 9727524

(51) Int. Cl.[7] .................................................. A61K 31/40
(52) U.S. Cl. ............................................................ 514/422
(58) Field of Search .............................................. 514/422

(56) References Cited

U.S. PATENT DOCUMENTS

| | | |
|---|---|---|
| 5,260,329 | 11/1993 | Mongelli et al. . |
| 5,420,296 | 5/1995 | Mongelli et al. . |
| 5,534,539 | 7/1996 | Mongelli et al. . |
| 5,593,976 | 1/1997 | Mongelli et al. . |
| 5,859,046 | 1/1999 | Alzani et al. . |

Primary Examiner—William R. A. Jarvis
Assistant Examiner—Vickie Kim
(74) Attorney, Agent, or Firm—Oblon, Spivak, McClelland, Maier & Neustadt, P.C.

(57) ABSTRACT

A pharmaceutical composition for use in antineoplastic therapy in mammals, including humans, comprising a biologically active ureido compound of formula (I)

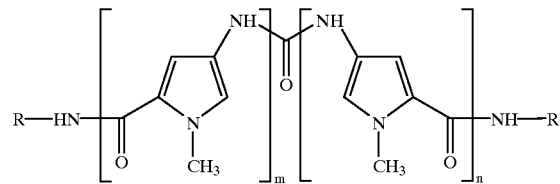

(I)

wherein each of m and n, being the same, is an integer of 1 to 3; and each of the R groups, which are the same, is a naphthyl group substituted by 1 to 3 sulfonic groups, or a pharmaceutically acceptable salt thereof, and an antineoplastic agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor, and a pharmaceutically acceptable carrier or excipient, in amounts effective to produce a synergistic antineoplastic effect, is provided herein.

11 Claims, No Drawings

SYNERGISTIC ANTITUMOR COMPOSITION CONTAINING A NAPHTHALENSULPHONIC ACID DERIVATIVE

This application is a 371 of PCT/EP98/08159 filed on Dec. 12, 1998.

FIELD OF THE INVENTION

The present invention relates in general in the field of cancer and, more particularly, provides an antitumor composition comprising a cytostatic agent and a biologically active ureido compound, having a synergistic antineoplastic effect.

BACKGROUND OF THE INVENTION

Neoplastic diseases in humans are recognized throughout the world as being serious and oftentimes life-threatening conditions. These neoplastic diseases, which are characterized by rapidly-proliferating cell growth, have been and continue to be the subject of worldwide research efforts directed toward the identification of therapeutic agents which are effective in the treatment of patients suffering therefrom. Effective therapeutic agents can be characterized as those which prolong the survival of the patients, which inhibit the rapidly-proliferating cell growth associated with the neoplasm, or which effect a regression of the neoplasm. Research in this area is primarily focused toward identifying agents which would be therapeutically effective in humans. Typically, compounds are tested for antineoplastic activity in small mammals, such as mice, in experiments designed to be predictive of antineoplastic activity not only in those animals but also in humans against specific neoplastic disease states. The present invention concerns a method for treating tumors utilizing a combination of known antitumor agents which exert their efficacy through inhibition of tumor cells proliferation (cytotoxic agents) with known not-cytotoxic ureido compounds which exert their efficacy through inhibition of blood vessel formation (angiogenesis).

It is a recognized phenomenon that angiogenesis is a fundamental requisite for solid tumor growth and metastatic spread. Angiogenesis is started when tumor cells produce angiogenic factors which stimulate quiescent endothelial cells to proliferate, destroy the basal membrane, migrate, adhere and proliferate to form new capillaries. As a consequence, inhibitors of angiogenesis will block tumor growth; although no definitive clinical response is presently available on the activity of the angiogenesis inhibitors undergoing clinical trials, experimental evidence indicates that modulation of angiogenesis alone may be insufficient to efficiently control tumor growth and metastatic spread. It is thus conceivable that combined therapy with non toxic inhibitors of angiogenesis and cytotoxic agents can represent a new effective clinical regimen.

Biologically active compounds known from WO 91/10649 inhibit angiogenesis through making a complex with growth factors and angiogenic polypeptides such as basic fibroblast growth factor, insulin growth factor-1 and hepatocyte growth factor. They do not inhibit tumor cells proliferation, and administered by intravenous (iv), intraperitoneal (ip), subcutaneous (sc) and oral route inhibit in mice angiogenesis induced by growth/angiogenic factors and the growth of transplanted human and murine tumors.

It has now been found that in treating a patient affected with certain neoplastic disease states, conjunctive therapy with a biologically active compound known from WO 91/10649 and a cytotoxic agent, will provide a synergistic antineoplastic effect.

A synergistic effect is achieved when a greater antineoplastic effect results with a conjunctive therapy than use of either drug alone, thus giving a superadditive antineoplastic effect. One advantage of conjunctive therapy with a synergistic effect is that lower dosages of the antineoplastic agent may be used so that the therapeutic index is increased and toxic side effects are reduced.

DESCRIPTION OF THE INVENTION

The present invention provides, in a first aspect, a pharmaceutical composition for use in antineoplastic therapy in mammals, including humans, comprising a biologically active ureido compound of formula (I)

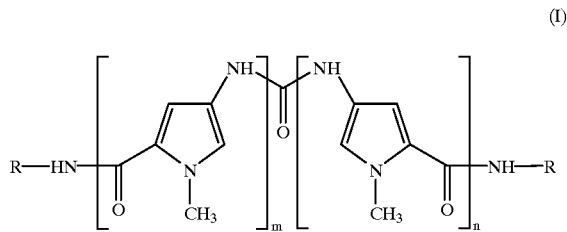

wherein
each of m and n, being the same, is an integer of 1 to 3; and each of the R groups, which are the same, is a naphthyl group substituted by 1 to 3 sulfonic groups, or a pharmaceutically acceptable salt thereof, and an antineoplastic agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor, and a pharmaceutically acceptable carrier or excipient, in amounts effective to produce a synergistic antineoplastic effect.

The present invention also provides a product comprising synergistic amounts of a biologically active ureido compound of formula (I), as defined above, or a pharmaceutically acceptable salt thereof, and an antineoplastic agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor, as a combined preparation for simultaneous, separate or sequential use in antitumor therapy.

A further aspect of the present invention is to provide a method of treating a mammal including humans, suffering from a neoplastic disease state comprising administering to said mammal a biologically active ureido compound of formula (I), as defined above, or a pharmaceutically acceptable salt thereof, and an antineoplastic agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor, in amounts effective to produce a synergistic antineoplastic effect.

The present invention also provides a method for lowering the side effects caused by antineoplastic therapy with an antineoplastic agent in mammals, including humans, in need thereof, the method comprising administering to said mammal a combination preparation comprising an antineoplastic agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor, and a biologically active ureido compound of formula (I), as defined above, or a pharmaceutically acceptable salt thereof, in amounts producing a synergistic antineoplastic effect.

Preferred compounds of formula (I) are the compounds wherein m and n are each 2 and each of the R groups are as defined above, and the pharmaceutically acceptable salts thereof.

Examples of specific preferred compounds of formula (I) are:

7,7'-(carbonyl-bis(imino-N-methyl-4,2-pyrrolecarbonyl-imino(N-methyl-4,2-pyrrole)carbonylimino))bis(3,5-naphthalendisulfonic acid);

7'-(carbonyl-bis(imino-N-methyl-4,2-pyrrolecarbonyl-imino(N-methyl-4,2-pyrrole)carbonylimino))bis(3,6-naphthalendisulfonic acid);

7,7'-(carbonyl-bis(imino-N-methyl-4,2-pyrrolecarbonyl-imino(N-methyl-4,2-pyrrole) carbonylimino))bis (1,3,5-naphthalentrisulfonic acid);

8,8'-(carbonyl-bis(imino-N-methyl-4,2-pyrrolecarbonyl-imino(N-methyl-4,2-pyrrole) carbonylimino))bis (1,3,6-naphthalentrisultonic acid);

7,7'-(carbonyl-bis(imino-N-methyl-4,2-pyrrolecarbonyl-imino(N-methyl-4,2-pyrrole) carbonylimino)) bis (1,3-naphthalendisulfonic acid);

7,7'-(carbonyl-bis(imino-N-methyl-4,2-pyrrolecarbonyl-imino(N-methyl-4,2-pyrrole) carbonylimino))bis (2,4-naphthalendisulfonic acid);

8,8'-(carbonyl-bis(imino-N-methyl-4,2-pyrrolecarbonyl-imino(N-methyl-4,2-pyrrole)carbonylimino))bis(2,4-naphthalendisulfonic acid);

8,8'-(carbonyl-bis(imino-N-methyl-4,2-pyrrolecarbonyl-imino(N-methyl-4,2-pyrrole)carbonylimino))bis(1,3,5-naphthalentrisulfonic acid);

8,8'-(carbonyl-bis(imino-N-methyl-4,2-pyrrolecarbonyl-imino(N-methyl-4,2-pyrrole) carbonylimino))bis(5-naphthalensulfonic acid);

8,8'-(carbonyl-bis(imino-N-methyl-4,2-pyrrolecarbonyl-imino(N-methyl-4,2-pyrrole)carbonylimino))bis(1,3-naphthalendisulfonic acid);

8,8'-(carbonyl-bis(imino-N-methyl-4,2-pyrrolecarbonyl-imino(N-methyl-4,2-pyrrole)carbonylimino))bis(3,5-naphthalendisulfonic acid);

8,8'-(carbonyl-bis(imino-N-methyl-4,2-pyrrolecarbonyl-imino(N-methyl-4,2-pyrrole)carbonylimino))bis(1,5-naphthalendisulfonic acid);

8,8'-(carbonyl-bis(imino-N-methyl-4,2-pyrrolecarbonyl-imino(N-methyl-4,2-pyrrole)carbonylimino))bis(3-naphthalensulfonic acid);

8,8'-(carbonyl-bis(imino-N-methyl-4,2-pyrrolecarbonyl-imino(N-methyl-4,2-pyrrole)carbonylimino))bis(1-naphthalensulfonic acid);

2,2'-(carbonyl-bis(imino-N-methyl-4,2-pyrrolecarbonyl-imino(N-methyl-4,2-pyrrole)carbonylimino))bis(1,5-naphthalendisulfonic acid);

7,7'-(carbonyl-bis(imino-N-methyl-4,2-pyrrolecarbonyl-imino(N-methyl-4,2-pyrrole)carbonylimino))bis(1,6-naphthalendisulfonic acid);

7,7'-(carbonyl-bis(imino-N-methyl-4,2-pyrrolecarbonyl-imino(N-methyl-4,2-pyrrole)carbonylimino))bis(2,6-naphthalendisulfonic acid);

7,7'-(carbonyl-bis(imino-N-methyl-4,2-pyrrolecarbonyl-imino(N-methyl-4,2-pyrrole)carbonylimino))bis(1,5-naphthalendisulfonic acid);

7,7'-(carbonyl-bis(imino-N-methyl-4,2-pyrrolecarbonyl-imino(N-methyl-4,2-pyrrole)carbonylimino))bis(2,5-naphthalendisulfonic acid);

7,7'-(carbonyl-bis(imino-N-methyl-4,2-pyrrolecarbonyl-imino(N-methyl-4,2-pyrrole)carbonylimino))bis(2,3-naphthalendisulfonic acid);

8,8'-(carbonyl-bis(imino-N-methyl-4,2-pyrrolecarbonyl-imino(N-methyl-4,2-pyrrole)carbonylimino))bis(1,6-naphthalendisulfonic acid);

8,8'-(carbonyl-bis(imino-N-methyl-4,2-pyrrolecarbonyl-imino(N-methyl-4,2-pyrrole)carbonylimino))bis(2,6-naphthalendisulfonic acid);

8,8'-(carbonyl-bis(imino-N-methyl-4,2-pyrrolecarbonyl-imino(N-methyl-4,2-pyrrole)carbonylimino))bis(2,5-naphthalendisulfonic acid);

8,8'-(carbonyl-bis(imino-N-methyl-4,2-pyrrolecarbonyl-imino(N-methyl-4,2-pyrrole)carbonylimino))bis(3,6-naphthalendisulfonic acid);

8,8'-(carbonyl-bis(imino-N-methyl-4,2-pyrrolecarbonyl-imino(N-methyl-4,2-pyrrole)carbonylimino))bis(2,3,5-naphthalentrisulfonic acid);

8,8'-(carbonyl-bis(imino-N-methyl-4,2-pyrrolecarbonyl-imino(N-methyl-4,2-pyrrole)carbonylimino))bis(1,4,6-naphthalentrisulfonic acid);

8,8'-(carbonyl-bis(imino-N-methyl-4,2-pyrrolecarbonyl-imino(N-methyl-4,2-pyrrole)carbonylimino))bis(2,4,6-naphthalentrisulfonic acid);

7,7'-(carbonyl-bis(imino-N-methyl-4,2-pyrrolecarbonyl-imino(N-methyl-4,2-pyrrole)carbonylimino))bis(1-naphthalensulfonic acid);

7,7'-(carbonyl-bis(imino-N-methyl-4,2-pyrrolecarbonyl-imino(N-methyl-4,2-pyrrole)carbonylimino))bis(2-naphthalensulfonic acid);

7,7'-(carbonyl-bis(imino-N-methyl-4,2-pyrrolecarbonyl-imino(N-methyl-4,2-pyrrole)carbonylimino))bis(3-naphthalensulfonic acid);

7,7'-(carbonyl-bis(imino-N-methyl-4,2-pyrrolecarbonyl-imino(N-methyl-4,2-pyrrole)carbonylimino))bis(4-naphthalensulfonic acid);

7,7'-(carbonyl-bis(imino-N-methyl-4,2-pyrrolecarbonyl-imino(N-methyl-4,2-pyrrole)carbonylimino))bis(1,4,6-naphthalentrisulfonic acid);

7,7'-(carbonyl-bis(imino-N-methyl-4,2-pyrrolecarbonyl-imino(N-methyl-4,2-pyrrole)carbonylimino))bis(1,3,6-naphthalentrisulfonic acid);

7,7'-(carbonyl-bis(imino-N-methyl-4,2-pyrrolecarbonyl-imino(N-methyl-4,2-pyrrole)carbonylimino))bis(2,4,6-naphthalentrisulfonic acid);

7,7'-(carbonyl-bis(imino-N-methyl-4,2-pyrrolecarbonyl-imino(N-methyl-4,2-pyrrole)carbonylimino))bis(2,3,5-naphthalentrisulfonic acid);

and the pharmaceutically acceptable salts thereof.

Particularly preferred compounds of formula (I) are:

7,7'-(carbonyl-bis(imino-N-methyl-4,2-pyrrolecarbonyl-imino(N-methyl-4,2-pyrrole)carbonylimino))bis(1,3-naphthalendisulfonic acid); and 2,2'-(carbonyl-bis(imino-N-methyl-4,2-pyrrolecarbonyl-imino(N-methyl-4,2-pyrrole)carbonylimino))bis(1,5-naphthalendisulfonic acid);

and the pharmaceutically acceptable salts thereof.

Examples of specific antineoplastic agents, according to the invention, which are administered with a biologically active ureido compound of formula (I), are:

vincristine, vinblastine, etoposide, tallimustine-amidoxime, i.e. 3-(1-methyl-4-(1-methyl-4-(1-methyl-4-(4,N,N-bis(2-chloroethyl)aminobenzene-1-carboxamido)pyrrole-2-carboxamido)pyrrole-2-carboxamido)pyrrole-2-carboxamido)proprionamidoxime, (2S-RR-4E)-1,3-dihydroxy-2-tetradecanoylamido-4-octadecene, paclitaxel, docetaxel, 7-epitaxol, 7-epitaxotere, epirubicin, idarubicin, 4'-iodoxorubicin, daunorubicin, actinomicin D, bleomycin, plycamicin, mitomycin, camptothecin, 9-aminocamptothecin, irinotecan (CPT 11), topotecan, metotrexate, cytarabine, azauridine, azarabine, fluorodeoxyuridine, deoxycoformycin, mercaptopurine, cisplatin and carboplatin. In particular they are epirubicin, 9-aminocamptothecin and irinotecan.

As already said, the invention includes within its scope also the pharmaceutically acceptable salts of the compounds of formula (I). Examples of pharmaceutically acceptable salts are either those with inorganic bases, such as sodium, potassium, calcium and aluminum hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and other acceptable organic amines. Sodium and potassium salts are preferred.

PHARMACOLOGY

As stated above the present inventor has discovered that the effect of a cytotoxic agent is significantly increased, without a parallel increased toxicity, by co-administering it with a non-cytotoxic ureido derivative of the formula (1) as herein defined. The superadditive actions of the combination preparations of the present invention are shown for instance by the following in vitro and in vivo tests, which are intended to illustrate but not to limit the present invention.

Compound 7'-(carbonyl-bis(imino-N-methyl-4,2-pyrrolecarbonyl-imino(N-methyl-4,2-pyrrole)carbonylimino))bis(1,3-naphtalen-disulfonic acid) tetrasodium salt (internal code PNU 145156E) was chosen as a representative compound of the non-cytotoxic ureido derivatives of formula (I) as herein defined.

Five cytotoxic agents: paclitaxel (TX), cisplatin (CIS), etoposide (VP-16) and two camptothecin derivatives, irinotecan (CPT-11) and 9-aminocamptothecin (9-AC) were selected as representatives of cytotoxic agents acting via different modes of action:

TX is a tubulin depolymerization inhibitor, CIS is a DNA-binding agent, VP-16 is a topoisomerase II inhibitor and CPT-11 and 9AC are two semisynthetic camptothecin derivatives, which inhibit topoisomerase I.

The combinations were assayed in vitro on M5076 murine reticulosarcoma cells and in vivo on the same tumor cells implanted intramuscularly.

IN VITRO RESULTS

Tumor cells were treated 72 h at 37° C., in a humidified athmosphere of 5% $CO_2$ with a fixed concentration of PNU 145156E and graded concentrations of cytotoxic compounds; results are reported as % cell growth, that is percentage of surviving cells vs untreated control.

Table 1 shows that the antiproliferative activity of TX, CIS, VP-16, 9-AC and SN-38 (the active metabolite of CPT-11) is unchanged in the presence of PNU 145156E.

TABLE 1

| | | % CELL GROWTH ± S.E. | |
|---|---|---|---|
| | | PNU 145156E 0 ng/ml | PNU 145156E 50000 ng/ml |
| PACLITAXEL | 100 | 1 ± 1 | 2 ± 0 |
| ng/ml | 25 | 50 ± 7 | 43 ± 1 |
| | 6.25 | 89 ± 1 | 87 ± 14 |
| | 0 | 100 | 85 ± 0 |
| CIS | 200 | 9 ± 5 | 4 ± 1 |
| ng/ml | 40 | 52 ± 7 | 46 ± 3 |
| | 8 | 91 ± 3 | 83 ± 7 |
| | 0 | 100 | 88 ± 3 |
| VP16 | 100 | 15 ± 7 | 9 ± 4 |
| ng/ml | 20 | 77 ± 5 | 66 ± 8 |
| | 4 | 96 ± 8 | 91 ± 2 |
| | 0 | 100 | 92 ± 5 |
| 9-AC | 40 | 7 ± 2 | 8 ± 3 |
| ng/ml | 10 | 28 ± 2 | 29 ± 9 |
| | 2.5 | 88 ± 10 | 76 ± 6 |
| | 0 | 100 | 92 ± 14 |
| SN-38 | 35 | 5 ± 1 | 5 ± 2 |
| ng/ml | 12.5 | 19 ± 2 | 25 ± 7 |
| | 6.5 | 75 ± 5 | 74 ± 7 |
| | 0 | 100 | 89 ± 19 |

IN VIVO RESULTS

Mice C57BL/6 were implanted with M5076 murine reticulosarcoma cells. PNU 145156E was administered ip 2 h prior to cytotoxic drugs administered iv starting treatment 24 h after tumor implant. Treatments were performed at days 1, 4, 7 and 11.

The antitumor activity was calculated in terms of:

% AUC: inhibition of tumor growth

T/C %: percentage of median increase in survival time

TGD: tumor growth delay

The A.U.C. (area under the curve) of the tumor growth was calculated by using the trapezoidal method, and is referred to the measurement of tumor growth performed one week after the last treatment. The percentage of inhibition (% A.U.C.) was calculated using the following formula:

$$100 - \frac{\text{A.U.C. tumor growth treated mice}}{\text{A.U.C. tumor growth control mice}} \times 100$$

The percentage of increase in survival time (T/C%) was calculated using the following formula:

$$\frac{\text{median survival time treated mice}}{\text{median survival time control mice}} \times 100$$

Mice were monitored according to guidelines and sacrificed when tumor weight exceeded 10% body weight. Tumor growth delay (TGD) is the time, in days, to reach one gram of tumor weight in treated animals as compared to control animals.

The toxicological evaluation was performed in terms of body weight loss and spleen and liver reduction.

Evaluation of statistical significance was performed as follows: Student's Test for cytotoxic activity, Two-Way Anova for increase in survival time (T/C %) with combined treatment in comparison to the increase exerted separately by the two drugs, Tukey Test for tumor weight reduction (AUC % inhibition) with combined treatment in comparison to the reduction exerted separately by the two drugs.

The criterion for statistical significance was the 0.01 level (^)

Results in Table 2 indicate that the combined treatment with TX and PNU 145156E results into 100% AUC inhibition of tumor growth and increased TGD (18–23 days).

At both doses of TX, the reduction of tumor weight is statistically significant. Marginal effect is observed in terms of increased survival time. No increased toxicity is observed.

TABLE 2 combination with TX

| Treatment group | Tumor weight (gr) | A.U.C. % inhib. | TGD | T/C % | Toxic/ total mice |
|---|---|---|---|---|---|
| TX 33 mg/kg | 2.34 ± 0.9 | 77 | 8 | 108 | 0/10 |
| TX 40 mg/kg | 1.3 ± 0.7 | 93 | 9 | 118 | 0/10 |
| PNU 145156E 100 mg/kg | 1.45 ± 0.7 | 88 | 9 | 121 | 0/10 |
| PNU 145156E + TX 33 mg/kg | 0.07 ± 0.00.5 | 100 | 18 | 134 | 0/10 |
| PNU 145156E + TX 40 mg/kg | 0.01 ± 0.001 | 100 | 23 | 143 | 0/10 |

Results in Table 3 indicate that the combined treatment with CIS and PNU results into a statistically significant reduction of tumor weight and increased TGD (32 days). No increased toxicity is observed.

TABLE 3 combination with CIS

| Treatment group | Tumor weight (gr) | A.U.C. % inhib. | TGD | T/C % | Toxic/ total mice |
|---|---|---|---|---|---|
| CIS 6 mg/kg | 1.1 ± 0.1 | 75 | 11 | 130 | 0/10 |
| PNU 145156E 100 mg/kg | 2.63 ± 0.8 | 85 | 10 | 141 | 0/10 |
| PNU 145156E + CIS | 0.35 ± 0.07 | 100 | 32 | 173 | 0/11 |

Results in Table 4 indicate that the combination with VP-16 results into a statistically significant reduction of tumor weight and increased TGD (28 days). Statistically significant effect is also observed in terms of increased survival time (195). No increased toxicity is observed.

TABLE 4 combination with VP-16

| Treatment group | Tumor weight (gr) | A.U.C. % inhib. | TGD | T/C % | Toxic/ total mice |
|---|---|---|---|---|---|
| VP-16 15 mg/kg | 2.86 ± 0.8 | 90 | 12 | 130 | 0/9 |
| PNU 145156E 100 mg/kg | 1.4 ± 0.7 | 90 | 16 | 148 | 0/9 |
| PNU 145156E + P-16 | 0.45 ± 0.2 | 100 | 28 | 195 ^ | 0/9 |

Results in Table 5 indicate that the combination with 9AC results into a statistically significant increased reduction of tumor weight and increased TGD (13–15 days) No increased toxicity is observed.

TABLE 5 combination with 9AC

| Treatment group | Tumor weight (gr) | A.U.C. % inhib. | TGD | T/C % | Toxic/ total mice |
|---|---|---|---|---|---|
| 9AC 2.5 mg/kg | 2.4 ± 0.9 | 45 | 5 | 121 | 0/10 |
| 9AC 3 mg/kg | 2.13 ± 0.8 | 48 | 6 | 125 | 0/10 |
| 9AC 3.5 mg/kg | 1.58 ± 0.6 | 68 | 8 | 128 | 1/10 |
| PNU 145156E + 100 mg/kg | 1.4 ± 0.7 | 75 | 9 | 121 | 0/10 |
| PNU 145156E + 9AC 2.5 mg/kg | 0.2 ± 0.01 | 96 | 13 | 140 | 0/10 |
| PNU 145156E + 9AC 3 mg/kg | 0.14 ± 0.07 | 100 | 14 | 147 | 1/9 |
| PNU 145156E + 9AC 3.5 mg/kg | 0.05 +− 0.001 | 100 | 15 | 140 | 1/9 |

Results in Table 6 indicate that the combination with CPT-11 results into a statistically significant reduction of tumor weight and increased TGD (>45 days). Statistically significant effect is also observed in terms of increased survival time (>250). No increased toxicity is observed.

TABLE 6 combination with CPT-11

| Treatment group | Tumor weight (gr) | A.U.C. % inhib. | TGD | T/C % | Toxic/ total mice |
|---|---|---|---|---|---|
| CPT-11 60 mg/kg | 0.05 ± 0.2 | 100 | 34 | 215 | 0/8 |
| PNU 145156E 100 mg/kg | 1.7 ± 0.65 | 90 | 16 | 148 | 0/8 |
| PNU 145156E + CPT-11 | 0 ± 0 | 100 | >45 | >250 | 0/8 |

From the above test data the following facts can be appreciated:

The combined treatment of PNU 145156E with the five tested drugs is associated in all combinations with higher tumor growth inhibition and increased tumor growth delay in respect to treatment with one drug alone, with a significant increase in survival time in the combination with VP-16 and CPT-11.

The synergistic activity observed in vivo is clearly not related to any interference of PNU 145156E on the antiproliferative effect of the cytotoxic drugs, as evidenced by results showing that in vitro the cytotoxic activity of the five tested drugs is unchanged in the presence of PNU 145156E.

It is of note that no obvious increased general toxicity was ever observed with the combinations, as evaluated in terms of early deaths or gross pathological findings at necropsy.

These results support the utilization of an ureido compound of formula (I), as herein defined, in therapy in combination with cytotoxic drugs.

In the combination preparations, pharmaceutical compositions and method of treatment, according to the present invention, one or more biologically active ureido compounds of formula (I) may be used at the same time, however only one compound of formula (I), or a pharmaceutically acceptable salt thereof, is preferably used.

The term "antineoplastic agent" as used herein refers both to a single antitumor drug and "cocktails" i.e. a mixture of such drugs according to the clinical practice.

The combination preparation according to the invention can also include combination packs or compositions in which the constituents are placed side by side and can therefore be administered simultaneously, separately or sequentially to one and the same mammal, including humans.

The term "neoplastic disease state" as used herein refers to an abnormal state or condition characterized by rapidly proliferating cell growth or neoplasm. Neoplastic disease states for which conjunctive therapy according to the present invention will be particularly useful include: Leukemias such as, but not limited to, acute lymphoblastic, chronic lymphocytic, acute myoblastic and chronic mylocytic; Carcinomas, such as, but not limited to, those of the cervix, oesophagus, stomach, such as, but not limited to, oesteroma, oesterosarcoma, lepoma, liposarcoma, hemangioma and hemangiosarcoma; Melanomas, including amelanotic and melanotic; and mixed types of neoplasias such as, but not limited to, carcinosarcoma, lymphoid tissue type, follicular reticulum, cell sarcoma, and Hodgkins Disease. Of course, one skilled in the art will recognize that not every combination of conjunctive therapy according to the present invention will be equally effective against each of the neoplastic disease states. Selection of the most appropriate combination is within the ability of one of ordinary skill in the art and will depend on a variety of factors including assessment of results obtained in standard animal cancer models and the effectiveness of the individual agents as monotherapy in treating particular neoplastic disease states. Conjunctive therapy may result in lowered doses of one or more of the antineoplastic agents.

For example, conjunctive therapy with an ureido compound of formula (I) and vinblastin will be particularly effective in the treatment of a patient afflicted with leukemia, carcinoma, lymphoma or osteosarcoma.

Conjunctive therapy with an ureido compound of formula (I) and cisplatin will be particularly effective in the treatment of a patient afflicted with carcinoma, testicular teratoma or ovarian carcinoma.

Conjunctive therapy with an ureido compound of formula (I) and epirubicin will be particularly effective in the treatment of a patient afflicted with breast carcinoma, leukemia, lymphoma or ovarian carcinoma.

Conjunctive therapy with an ureido compound of formula (I) and cytarabine will be particularly effective in the treatment of a patient afflicted with leukemia.

Conjunctive therapy with an ureido compound of formula (I) and CPT-11 or 9-aminocamptothecin will be particularly effective in the treatment of advanced colon and ovarian cancer.

As used herein, the term "effective antineoplastic amount" refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and does not necessarily indicates a total elimination of the neoplasm.

An effective antineoplastic amount of an ureido compound of formula (I) is expected to vary from about 0.5 to about 1000 mg pro dose 1–4 times a day The effective antineoplastic amounts of the various cytotoxic agents are well known and appreciated in the art. For example, an effective antineoplastic amount of vinblastine is expected to vary from about 3 mg/m$^2$/day to about 10 mg/m$^2$/day. An effective antineoplastic amount of cisplatin is expected to vary from about 20 mg/m$^2$/day to about 50 mg/m$^2$/day. An effective antineoplastic amount of cytarabine is expected to vary from about 1 mg/m$^2$/day to about 200 mg/m$^2$/day. An effective antineoplastic amount of 9-aminocamptothecin is expected to vary from about 0.5 mg/m$^2$/day to about 10 mg/m$^2$/day. An effective antineoplastic amount of irinotecan is expected to vary from about 50 mg/m$^2$/day to about 500 mg/m$^2$/day.

In effecting treatment of a patient afflicted with a disease state described above an ureido derivative of formula (I) can be administered in any form or mode which makes the compound bioavailable in effective amounts, including oral and parenteral routes. For example, it can be administered orally, subcutaneously, intraperitoneally, intramuscularly, intravenously, transdermally, intranasally, rectally, and the like. Oral administration is generally preferred. One skilled in the art of preparing formulations can readily select the proper form and mode of administration depending upon the particular circumstances, including the disease state to be treatment, the stage of the disease, the form of administration of the selected cytotoxic agent and the manner of co-administration selected.

For example, WO 91/10649 discloses the preparation of pharmaceutical compositions comprising an ureido compound of formula (I) and a suitable carrier or excipient. The selected antineoplastic agent can be administered in a manner as is well known and accepted for the particular agent. For example, vincristine, vinblastine, etoposide, tallimustine-amidoxime, i.e. 3-(1-methyl-4-(1-methyl-4-(1-methyl-4-(4,N,N-bis(2-chloroethyl)aminobenzene-1-carboxamido)pyrrole-2-carboxamido)pyrrole-2-carboxamido)pyrrole-2-carboxamido)proprionamidoxime, (2S-RR-4E)-1,3-dihydroxy-2-tetradecanoylamido-4-octadecene, paclitaxel, docetaxel, 7-epitaxol, 7-epitaxotere, epirubicin, idarubicin, 4'-iodoxorubicin, daunorubicin, actinomicin D, bleomycin, plycamicin, mitomycin, camptothecin, 9-aminocamptothecin, irinotecan (CPT 11), topotecan, metotrexate, cytarabine, azauridine, azarabine, fluorodeoxyuridine, deoxycoformycin, mercaptopurine, cisplatin and carboplatin, can be administered intravenously. Irinotecan, 9-aminocamptothecin and topotecan can also be administered by oral route.

FORMULATION EXAMPLE 1

Intramuscular Injection 40 mg/ml

An injectable pharmaceutical preparation can be manufactured by dissolving 40 g of 7,7'-(carbonyl-bis(imino-N-methyl-4,2-pyrrolecarbonylimino(N-methyl-4,2-pyrrole)carbonylimino)-bis(1,3-naphthalenedisulfonic acid) tetrasodium salt in water for injection (1000 ml) and sealing ampoules of 1–10 ml.

What is claimed is:

1. A pharmaceutical composition comprising 7,7'-(carbonyl-bis(imino-N-methyl-4,2-pyrrolecarbonyl-imino (N-methyl-4,2-pyrrole)carbonylimino))bis(1,3-naphthalendisulfonic acid) tetrasodium salt, and an antineoplastic agent selected from the group consisting of paclitaxel, cisplatin, etoposide, irinotecan, and 9-aminocamptothecin, in amounts effective to produce a synergistic antineoplastic effect.

2. A pharmaceutical composition according to claim 1, wherein the antineoplastic agent is paclitaxel.

3. A pharmaceutical composition according to claim 1, wherein the antineoplastic agent is cisplatin.

4. A pharmaceutical composition according to claim 1, wherein the antineoplastic agent is etoposide.

5. A pharmaceutical composition according to claim 1, wherein the antineoplastic agent is irinotecan.

6. A pharmaceutical composition according to claim 1, wherein the antineoplastic agent is 9-aminocamptothecin.

7. A method of treating a mammal, suffering from a neoplastic disease state selected from the group consisting of leukemia, carcinoma, lymphoma and osteosarcoma, comprising administering to said mammal a biologically active ureido compound of formula (I)

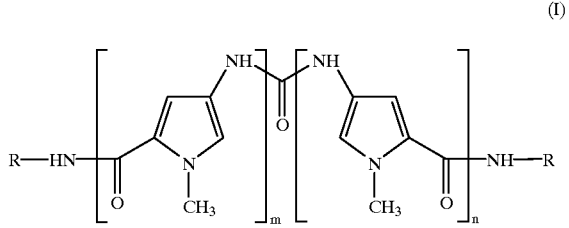

wherein
each of m and n, being the same, is an integer of 1 to 3; and each of the R groups, which are the same, is a naphthyl group substituted by 1 to 3 sulfonic groups, or a pharmaceutically acceptable salt thereof, and vinblastin in amounts effective to produce a synergistic antineoplastic effect.

8. A method of treating a mammal, suffering from a neoplastic disease state selected from the group consisting of carcinoma, testicular teratoma and ovarian carcinoma, comprising administering to said mammal a biologically active ureido compound of formula (I)

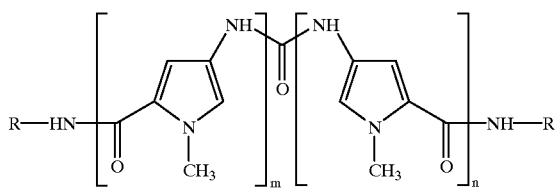

wherein
each of m and n, being the same, is an integer of 1 to 3; and each of the R groups, which are the same, is a naphthyl group substituted by 1 to 3 sulfonic groups, or a pharmaceutically acceptable salt thereof, and cisplatin in amounts effective to produce a synergistic antineoplastic effect.

9. A method of treating a mammal, suffering from a neoplastic disease state selected from the group consisting of breast carcinoma, leukemia, lymphoma and ovarian carcinoma, comprising administering to said mammal a biologically active ureido compound of formula (I)

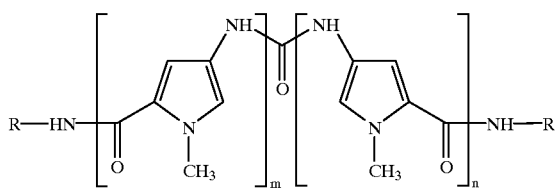

wherein
each of m and n, being the same, is an integer of 1 to 3; and each of the R groups, which are the same, is a naphthyl group substituted by 1 to 3 sulfonic groups, or a pharmaceutically acceptable salt thereof, and epirubicin in amounts effective to produce a synergistic antineoplastic effect.

10. A method of treating a mammal, suffering from a neoplastic disease state consisting of leukemia, comprising administering to said mammal a biologically active ureido compound of formula (I)

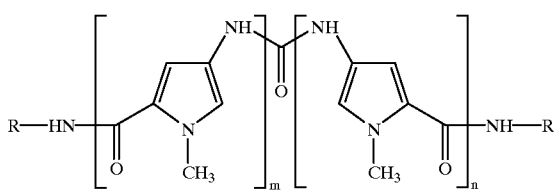

wherein
each of m and n, being the same, is an integer of 1 to 3; and each of the R groups, which are the same, is a naphthyl group substituted by 1 to 3 sulfonic groups, or a pharmaceutically acceptable salt thereof, and cytarabine in amounts effective to produce a synergistic antineoplastic effect.

11. A method of treating a mammal, suffering from a neoplastic disease state selected from the group consisting of advanced colon and ovarian cancer comprising administering to said mammal a biologically active ureido compound of formula (I)

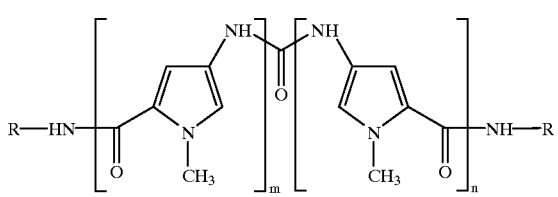

wherein
each of m and n, being the same, is an integer of 1 to 3; and each of the R groups, which are the same, is a naphthyl group substituted by 1 to 3 sulfonic groups, or a pharmaceutically acceptable salt thereof, and CPT-11 or 9-aminocamptothecin in amounts effective to produce a synergistic antineoplastic effect.

* * * * *